United States Patent [19]

Scrivo et al.

[11] 4,014,098
[45] Mar. 29, 1977

[54] FIBER OPTICS ELEMENT AND DENTAL HANDPIECE CONTAINING THE SAME

[75] Inventors: Leonard Scrivo, Tuckahoe; Warren Charles Vetter, Glendale, both of N.Y.

[73] Assignee: Vicon Products Corporation, Pelham Manor, N.Y.

[22] Filed: July 21, 1975

[21] Appl. No.: 597,191

Related U.S. Application Data

[62] Division of Ser. No. 360,919, May 16, 1973, Pat. No. 3,897,134.

[52] U.S. Cl. .................................................. 32/26
[51] Int. Cl.² .......................................... A61C 1/08
[58] Field of Search ................................. 32/27, 26

[56] References Cited

UNITED STATES PATENTS

| | | | |
|---|---|---|---|
| 3,789,506 | 2/1974 | Johns | 32/27 |
| 3,893,242 | 8/1975 | Lieb et al. | 32/27 |

*Primary Examiner*—Robert Peshock
*Attorney, Agent, or Firm*—Lerner, David, Littenberg & Samuel

[57] ABSTRACT

A fiber optics element is provided which includes a fiber optics bundle having at least two optical surfaces or faces and support means supporting at least a portion of the fiber optics bundle with one optical face in a desired initial position, and yieldable means cooperating with the fiber optics bundle to permit movement of said one optical face relative to its said initial position upon application of pressure to said one optical face.

In a preferred embodiment, the fiber optics element includes a fiber optics bundle having an optical surface or at each end, and is especially adapted for use in combination with a dental handpiece in a manner such that one optical face extends through the turbine housing portion of the dental handpiece. The fiber optics element further includes a tubular guide member, resilient support means in the form of a flexible tubular member, and a plunger assembly; the fiber optics bundle extends through each of the above components. The other optical face of the fiber optics element is adapted to be coupled under compression and in face to face alignment with a light emitting face of a second fiber optics bundle, which is connectable to a light source, to complete a light path to the light source.

A dental handpiece, such as a drill handpiece, including the above fiber optics element is also provided.

5 Claims, 6 Drawing Figures

FIBER OPTICS ELEMENT AND DENTAL HANDPIECE CONTAINING THE SAME

This is a division of application Ser. No. 360,919 filed May 16, 1973 and now U.S. Pat. No. 3,897,134 issued July 29, 1975.

FIELD OF THE INVENTION

This invention relates to a fiber optics element which is especially adapted for use in combination with medical or dental instruments, and to a dental handpiece containing such fiber optics element.

BACKGROUND OF THE INVENTION

Fiber optic illumination systems have now become a useful tool when employed in conjunction with dental instruments, such as mirrors, drills, or just as a source of illumination for working areas. Such illumination systems are disclosed in U.S. Pat. Nos. 2,539,828; 3,032,879; 3,397,457 and 3,638,013.

U.S. Pat. No. 3,397,457 discloses a dental drill which employs a fiber optic bundle which is attached to the turbine end of the drill, but does not actually protrude or extend through the turbine housing.

U.S. Pat. No. 3,638,093, discloses a dental apparatus utilizing fiber optics, one portion of said apparatus being a dental drill handpiece. The fiber optics bundle employed with the dental drill handpiece, as in U.S. Pat. No. 3,397,457, does not protrude through the turbine, housing but exits the handpiece in an area before the turbine housing.

Although a fiber optics system is employed in the aforedescribed dental apparatus to achieve increased illumination in the work area, maximum illumination is not achieved because the light emitting face of the fiber optics bundle does not protrude through the turbine housing portion of the drill. Instead, such light emitting face is disposed outside of the turbine housing and thus does not directly illuminate the work area. Furthermore, a portion of the fiber optics bundle employed in the above patents is attached to an external portion of the handpiece and thus is subject to being accidentally pulled away from the handpiece and severed from the remainder of the bundle.

SUMMARY OF THE INVENTION

In accordance with the present invention, a fiber optics element is provided, which is especially adapted for use in conjunction with medical and dental instruments, such as a dental handpiece. One optical face, in the form of a light emitting face, of a fiber optics bundle employed in the fiber optics element itself is completely retained in the dental handpiece and only protrudes through the turbine housing portion of the dental drill. Thus, there is no exposed portion of the fiber optics bundle or element at the working end of the dental handpiece except that portion which protrudes through the turbine housing. Accordingly, the fiber optics element cannot be accidentally pulled away from the remainder of the handpiece. Furthermore, such a fiber optics element when employed in conjunction with a dental handpiece provides light in the working area where it is most needed and permits increased acuity in areas which were never before clearly visualized in operative dentistry, especially in the oral posterior regions.

The fiber optics element of the invention generally comprises a fiber optics bundle having at least two optical surfaces or faces, support means supporting at least a portion of the fiber optics bundle with one optical face in a desired initial position, and yieldable means cooperating with the fiber optics bundle to permit movement of the one optical face relative to its said initial position, for example, upon application of pressure to the one optical face.

A preferred embodiment of the fiber optics element of the invention comprises a fiber optics bundle which includes a plurality of light conducting fibers, said bundle having first (distal) and second (proximal) end portions, each terminating in respective first and second optical faces; a first tubular guide member or protective sheath having first and second end portion; a resilient support means in the form of a flexible tubular member having first and second end portions; and yieldable means preferably in the form of a plunger assembly comprising a tubular plunger member havng first and second end portions, a stop element connected to said tubular plunger member between said first and second end portions thereof, a second tubular guide member having first and second end portions, disposed about said tubular plunger member and said stop element, and biasing means, such as spring means, disposed about said tubular plunger member between said stop element and said first end of said second tubular guide member. The first end portion of the second tubular guide member is of a smaller diameter than the stop element and the spring means. Thus, in such embodiment, the spring means can be disposed about the tubular plunger member in a channel formed between the stop element, the internal walls of the second tubular guide member and the first end of the second tubular guide member. The fiber optics bundle extends through the first tubular guide member, the flexible tubular member and the tubular plunger member.

The first end portion of the flexible tubular member is preferably in communication with the second end portion of the first tubular guide member and the second end potion of the flexible tubular member is preferably in communication with the first end portion of the tubular plunger member so that the fiber optics bundle is completely enclosed and protected except for the optical faces thereof.

The above fiber optics element is designed so that when the first and second tubular guide members are held in a rigid position, the tubular plunger member, including the fiber optics bundle portion therein, can be depressed into the second tubular guide member and held under tension.

Further, in accordance with the present invention, there is provided a dental drill handpiece which includes a head member defining a turbine housing, a turbine within the housing, a drive shaft extending outwardly from the turbine, a handle means comprising an elongated hollow shaft, and a fiber optics element as described above, disposed in the handle means and head member in a manner such that the optical face of the first (distal) end portion of the fiber optics bundle extends into and is rigidly retained by the head member. The second end porton of the fiber optics bundle (that is the proximal optical face) and the second end portion of the tubular plunger member (which is a part of the plunger assembly) extends rearwardly from the handle means. A drive air supply conduit as well as conduits or connections for exhaust air, irrigation air, and water, may also extend rearwardly from the non-working end of the handpiece or handle means.

The handle means will normally terminate in an end or joint member which includes a series of passages, namely a first passage of which is adapted to retain and rigidly hold at least a portion of the second tubular guide member so that at least a portion of the second end of the tubular plunger member extends rearwardly from the end member, and passages for air and water conduits described above.

The non-working end or handle means of the handpiece is adapted to be connected to corresponding conduits for air and water as well as to a second fiber optics bundle having an optical face at one end, all of which may be carried in one or more dental hoses, as will be described later. The other end of the second fiber optics bundle is connectable to a light source. Coupling means are provided to connect or couple the non-working end of the dental handpiece and associated conduits to the dental hose or hoses carrying said second fiber optics bundle and air and water conduits in a manner such as to rigidly retain the light emitting face of the second fiber optics bundle against the second optical face (proximal) of the first fiber optics bundle so that said optical faces of the fiber optics bundles are retained in face to face alignment with each other under compression by normal closure of the coupling means.

The afore-described fiber optics element of the invention may be employed as a source of illumination for and in conjunction with many types of medical and dental instruments such as laryngoscopes, endoscopes, boroscopes, dental drill handpieces, dental mirrors and the like as well as for any instruments, tools, devices and the like that require an illuminating source and where at least two fiber optics bundles must be connected to each other to complete a light path.

DETAILED DESCRIPTION OF THE INVENTION

Figure 1:
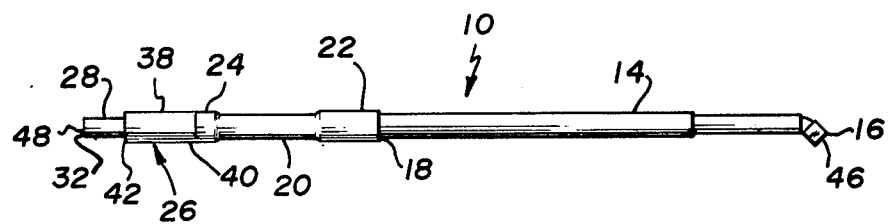
FIG. 1 is a side elevational view of a preferred fiber optics element in accordance with the present invention.
Figure 2:
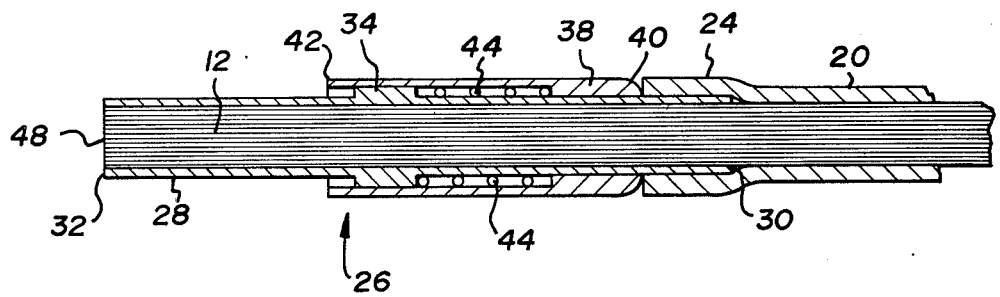
FIG. 2 is a cross sectional view of a portion of the fiber optics element shown in FIG. 1.

Referring now to the accompanying drawings in which like reference numerals refer to similar parts throughout, a preferred fiber optics element in accordance with the present invention, is shown in FIGS. 1 and 2 and is generally identified by the numeral 10. The element 10 includes a fiber optics bundle 12, which comprises a plurality of fibers as will be apparent to one skilled in the art. The element 10 also includes a first tubluar guide member or protective sheath 14 having a first end portion 16 and a second end portion 18, a portion of which is enclosed by resilient support means in the form of a flexible tubular member 20 which, in turn, has first and second end portions 22 and 24, respectively.

Yieldable means in the form of a plunger assembly, generally indicated by the numeral 26 is in communication with flexible tubular member 20 as shown in FIGS. 1 and 2. The plunger assembly 26 includes a tubular plunger member 28 having first and second end portions 30 and 32, respectively (more clearly shown in FIG. 2). The tubular plunger member 28 includes a stop element 34 which may be in the form of an annular shoulder, which in a preferred embodiment, is integral with or welded, for example, to the tubular plunger member 28 as shown. A second tubular guide member 38 having first and second end portions 40 and 42, respectively, is disposed about the tubular plunger member 28 and the stop element 34 as shown. Cylindrical spring means 44 (shown in FIG. 2) is disposed about the tubular plunger member 28 between the stop element 34 and the first end 40 of the second tubular guide member 38. As shown in FIG. 2, the internal diameter of the first end 40 of the second tubular guide member 38 is of a smaller diameter than the stop element 34 and the spring means 44, so that the spring means 44 actually is disposed in the channel formed between the stop element 34, the internal walls of the second tubular guide member 38 and the first end 40 of the second tubular guide member.

The fiber optics bundle 12 extends through the first tubular guide member 14, the flexible tubular member 20, and the tubular plunger member 28 with the ends 46 and 48 of the fiber optics bundle 12 terminating in optical faces.

As shown, the optical faces 46 and 48 of the fiber optics bundle 12 are flush with the end 16 of the first tubular guide member and the end 32 of the tubular plunger member, respectively. When the first and second tubular guide members, 14 and 38, respectively, are held in a rigid position, the tubular plunger member 28, including the fiber optics bundle portion therein, can be depressed into the second tubular guide member 38 and held therein under tension.

Figure 3:
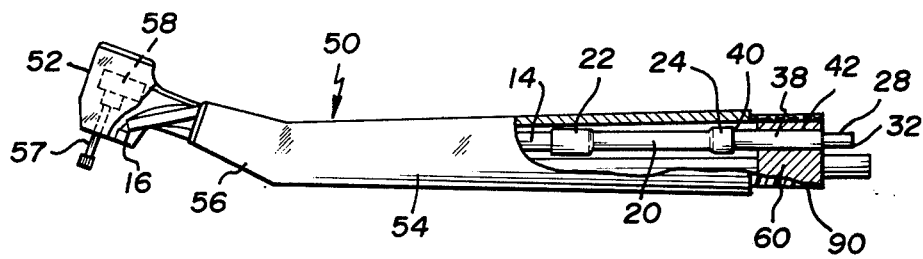
FIG. 3 is a side elevational view of a drill handpiece which includes the fiber optics element of FIG. 1 as shown in the portion which is broken away.

As shown in FIG. 1, the end 16 of the first tubular guide member 14 is hooked or angled so that when the element 10 is employed in a drill handpiece, such as shown in FIG. 3, the hooked end 46 of the fiber optics bundle will be positioned at a predetermined desired angle so as to afford maximum illumination to the work area.

The tubular guide members 14 and 38 as well as the tubular plunger member 28 can be constructed of any rigid material, such as a steel or a rigid plastic. The flexible tubular member 20 may be constructed of any flexible hose material, such as rubber hose or flexible plastic hose.

The stop element 34 which may be formed integral with the tubular plunger member 28 or may be fixedly secured thereto, can take the form of a metal or plastic annular shoulder or raised portion.

The fiber optics element 10 shown in FIGS. 1 and 2 can be employed in conjunction with a drill handpiece as shown in FIG. 3 wherein the drill handpiece is generally referred to by the numeral 50. The drill handpiece 50 is an air-driven drill comprising a head 52, a hollow main handle shell 54 and a joint member 60. The main handle section 54 is elongated and straight, with the forward section thereof 56 being tapered forwardly as shown. The taper forward section 56 extends through an obtuse angle and can take the form of a separable member threaded to the main handle section 54, and ends at a reduced diameter adjacent the head member 52, which allows the dentist to see the drill point.

The head 52 is mounted on the forward section 56 and houses an air drive turbine 58 (as indicated by the broken lines) which drives the drive shaft 57. The turbine 58 is powered by air supplied via air supply 80 and exhaust conduit 82 which communicate with the turbine and the head 52 and pass through the forward handle portion 56 and the main handle portion 54, not shown for purposes of drawing clarity.

The dental drill handpiece 50 also includes conduits for irrigation air 84 and water 86 which have outlets at the head 52, and extend rearwardly from the end of handle means 54.

Figure 4:
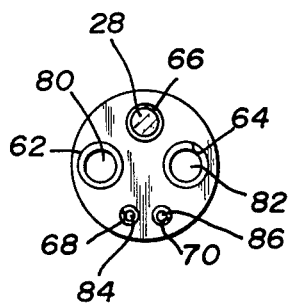
FIG. 4 is an end view of the drill handpiece as shown in FIG. 3.

Handle means 54 also includes end or joint member 60 which is also shown in FIG. 4 and preferably is in the form of a metallic or rigid plastic plug member. The joint member 60 which is press-fit into or otherwise retained by the handle means 54 includes axial passages for the air supply 62 the exhaust 64, the fiber optics bundle 66 as well as passages 68 for irrigation air, and 70 for water. These passages communicate with corresponding conduits or tubes extending from the handle means 54. As shown, the end of the handle means 54 is threaded 90 so that it may be employed to couple the handle 54 to flexible dental hose 72 shown in FIG. 5.

The fiber optics element 10 is positioned in the hollow shaft of the handle means 54 and 56 and head member 52 so that the light emitting face 46 of the fiber optics bundle 12 extends into and is rigidly retained by the head member 52. The second tubular guide member 38 is rigidly retained in passage 66 of the joint member 60 with a portion of the tubular plunger member 28 protruding beyond the joint member 60 as shown. The passage 66 is of a larger diameter than the diameter of the tubular plunger member 28 so that the end of the tubular plunger member 28 is free to move into and out of the passage 66.

Figure 5:
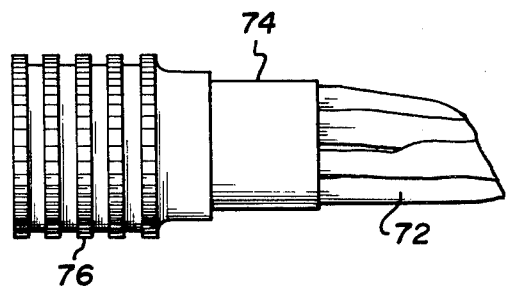
FIG. 5 is a side view of a dental handpiece hose which includes a fiber optics bundle and coupling means for coupling the hosed and conduits therein to the end of the handpiece shown in FIG. 3.
Figure 6:
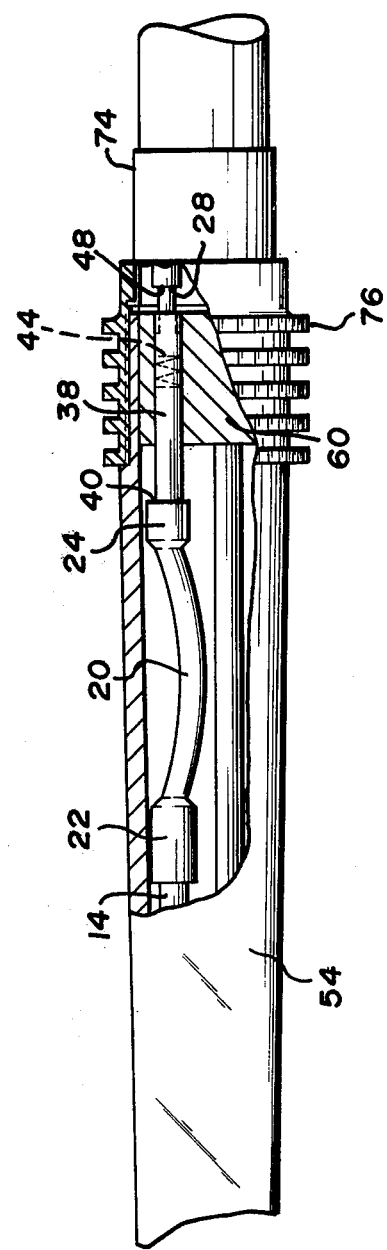
FIG. 6 is a side view, partially broken away, illustrating the drill handpiece and hose in their assembled relationship.

As shown in FIG. 5 flexible dental hose 72 is provided with a joint member or end plug 74 which includes holes or passages mating with the conduits protruding from the axial holes in the joint member 60. The end plug 74 is provided with a fitting 76 which is internally threaded so that the end plug 74 can be brought against the joint member 60 by the threaded fitting 76 thereby connecting up the corresponding passages in the handle 54 and flexible dental hose 72.

When the fitting 76 is screwed on to the handle means 54, the light emitting face of the fiber optics bundle located in the hose 72 is brought into contact with the optical face of the fiber optics bundle carried by the tubular plunger member 28. As the fitting is screwed into its closed position around handle means 54 to abut with the joint member 60, the optical face of the fiber optics bundle in the hose 72 directly contacts and presses against the light emitting face housed in the end 32 of the tubular plunger member 28 thereby causing the tubular plunger member and its associated optical face of the fiber optics bundle to be depressed into the second tubular guide member 38 and held there under compression, due to corresponding depression of the spring means 44. This action will cause the flexible tubular member 20 to flex slightly and take up the slack of the fiber optics bundle 12 without causing the bundle 12 to sever or in any way break.

When the fitting 76 is in its closed position, connecting the end plugs 74 and 60, the optical faces of the fiber optics bundle 12 located at the end of the tubular plunger member 28 and the optical face of the fiber optics bundle in hose 72 located in the end plug 74 will remain in direct contact and alignment in face to face relation with each other except when the fitting 76 is unscrewed and the end plugs 60 and 74 are allowed to separate from each other.

The end of the fiber optics bundle positioned in the dental hose 72, away from the end plug 74, will be connected to a suitable light source.

The dental hose 72 can be of any conventional construction and preferably will take the form of the hose described in copending U.S. application Ser. No. 196,350 filed Nov. 8, 1971 which includes a series of conduits for supply air, exhaust air, irrigation and water.

In operation, the fiber optics bundle in hose 72 is connected to a high intensity light source (not shown), air and water connections are made to the hose 72, and the dental drill handle 54 is secured to the hose 72 by means of the threaded fitting 76. The fitting 76 may be fitted with a gasket to insure that a good seal is maintained between the end plugs 60 and 74.

A light path from the light source to the head member 12 is established by virtue of securing the end plugs 60 and 74 together by means of the fitting 76, thereby bringing the light emitting face 48 of the fiber optics bundle 12 into direct contact and alignment with the light emitting face of the fiber optics bundle in the hose 72. The light proceeds from the light source through the fiber optics bundle in the hose 72 and the fiber optics bundle 12 to the optical face 46.

The light emitting face 46 is spaced from the drill point, but is in close proximity thereto so that the light beam is directed to the area of drilling.

The fiber optics bundle 12 in no way impairs the air and water passages in the drill handpiece 50 or in the dental hose 72 so that the proper drill speed is assured.

The fiber optics element of the invention may also be fashioned so as to have two or more optical faces, in the form of light emitting faces, at the distal end thereof. Thus, for example, the fiber optics bundle of said element can be branched at the distal end, with each branch protected in a protective sheath 14 and each end portion of each branch terminating in a light emitting face.

It will be understood that the afore-described plunger assembly may be comprised of embodiments other than that described with respect to the Figures.

Furthermore, as will be apparent to one skilled in the art, the biasing means of the tubular plunger assembly may comprise fluid biasing means or mechanical biasing means other than spring means.

It is to be understood that the present description has been by way of example only and is not intended as a limitation to the scope of the invention as defined by the appended claims.

What is claimed is:

1. A dental drill handpiece comprising:
   a head member defining a turbine within said housing;
   a drive shaft extending outwardly from said turbine;
   a handle means comprising an elongated hollow shaft attached to said head member;
   A fiber-optics element comprising a fiber-optics bundle having first and second end portions, terminating in first and second optical faces, respectively, a first tubular guide member disposed about a first portion of said fiber-optics bundle, a flexible tubular member disposed about a second portion of said fiber-optics bundle disposed adjacent to said first portion thereof, and a plunger assembly comprising a tubular plunger member disposed about a third portion of said fiber-optics bundle disposed adjacent to said second portion thereof, said third portion including said second optical face of said fiber-optics bundle, said plunger assembly further including a second tubular guide member comprising first and second end portions and being disposed about said tubular plunger member, said plunger member including a stop element disposed between said plunger member and said second tubular guide member, said first end portion of said second tubular guide member being of a diameter such that it cannot pass over said stop element, and said plunger assembly further comprises spring means disposed about said tubular plunger member and between said stop element and said first end portion of said second tubular guide member, and said flexible tubular member includes an overlapping end portion thereof which is disposed about said tubular plunger member such that said flexible tubular member is biased by said spring member into engagement with said first end portion of said second tubular guide member which first end portion thus serves as a stop for said flexible tubular member such that said fiber-optics element comprises a self-supported plunger assembly;

said fiber-optics element being disposed in said handle means and head member in a manner such that said first optical face of said fiber-optics bundle is rigidly retained by said head member and said second optical face of said fiber-optics bundle and said third portion of said fiber-optics bundle extends rearwardly from said handle means whereby the second optical face can be depressed into said second tubular guide member by pressing a third optical face against said second optical face to compress said spring and bend said flexible tubular member to maintain a biasing force on said second optical face tending to force said second optical face out of said second tubular guide member and into engagement with said third optical face.

2. The dental drill handpiece in accordance with claim 1 including in addition a second fiber optics bundle haing a first light emitting face at one end and the other end of which is connectable to a light source and coupling means adapted to rigidly retain said first light emitting face of second fiber optics bundle against the second optical face of said first fiber optics bundle so that said faces of said fiber optics bundles are retained in face to face alignment with each other by normal closure of said coupling means.

3. The dental drill handpiece in accordance with claim 1 wherein said hollow shaft terminates in a joint member which includes a first passage, and at least a portion of said yieldable means is rigidly retained in said first passage, with at least another portion of said yieldable means extending rearwardly from said joint member.

4. The dental handpiece in accordance with claim 3 including a second joint member for retaining said first light emitting face of said second fiber optics bundle, and said coupling means is retained on said second member.

5. The dental handpiece in accordance with claim 4 wherein said first joint member is externally threaded and said coupling means comprises an internally threaded fitting which is adapted to be secured to said first joint member and bring the second optical face of said first fiber optics bundle and said first light emitting face of said second fiber optics bundle in abutting aligned contact upon normal closure of said coupling means.

* * * * *